US008877251B2

(12) United States Patent
Mueller-Walz

(10) Patent No.: US 8,877,251 B2
(45) Date of Patent: Nov. 4, 2014

(54) POWDER COMPOSITIONS FOR INHALATION

(75) Inventor: Rudi Mueller-Walz, Schopfheim (DE)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 13/604,280

(22) Filed: Sep. 5, 2012

(65) Prior Publication Data

US 2012/0328704 A1 Dec. 27, 2012

Related U.S. Application Data

(63) Continuation of application No. 12/086,345, filed as application No. PCT/EP2006/011941 on Dec. 12, 2006, now abandoned.

(30) Foreign Application Priority Data

Dec. 12, 2005 (GB) .................................. 0525254.9

(51) Int. Cl.
| A61P 11/08 | (2006.01) |
| A61K 9/14 | (2006.01) |
| A61K 47/00 | (2006.01) |
| A61K 9/00 | (2006.01) |
| A61K 38/28 | (2006.01) |
| A61K 39/395 | (2006.01) |

(52) U.S. Cl.
CPC .................... *A61K 9/0075* (2013.01)
USPC ........... 424/498; 514/304; 514/291; 514/424; 424/490; 424/493; 424/489

(58) Field of Classification Search
CPC ..................................................... A61K 9/0075
See application file for complete search history.

(56) References Cited

U.S. PATENT DOCUMENTS

| 4,672,108 | A | 6/1987 | Kung et al. |
| 5,830,853 | A * | 11/1998 | Backstrom et al. ............ 514/6.5 |
| 5,874,063 | A | 2/1999 | Briggner et al. |
| 6,182,655 | B1 | 2/2001 | Keller et al. |
| 6,528,096 | B1 | 3/2003 | Musa et al. |
| 6,645,466 | B1 | 11/2003 | Keller et al. |
| 7,186,401 | B2 | 3/2007 | Keller et al. |
| 8,211,405 | B2 | 7/2012 | Mueller-Walz et al. |
| 8,246,935 | B2 | 8/2012 | Mueller-Walz et al. |
| 2003/0175214 | A1 | 9/2003 | Staniforth et al. |
| 2006/0147389 | A1* | 7/2006 | Staniforth et al. ............ 424/46 |
| 2007/0071690 | A1 | 3/2007 | Mueller-Walz et al. |
| 2010/0144625 | A1 | 6/2010 | Mueller-Walz |
| 2011/0114092 | A1 | 5/2011 | Keller et al. |

FOREIGN PATENT DOCUMENTS

| DE | 98022 A1 | 6/1973 |
| EP | 0239798 A1 | 10/1987 |
| EP | 0272772 A2 | 6/1988 |
| EP | 01129705 A1 | 9/2001 |
| JP | 2002529498 A | 9/2002 |
| JP | 2003034652 A | 2/2003 |
| WO | WO-9623485 A1 | 8/1996 |
| WO | WO-9703649 A1 | 2/1997 |
| WO | WO-9948476 A1 | 9/1999 |
| WO | WO-0028979 A1 | 5/2000 |
| WO | WO-0178693 A2 | 10/2001 |
| WO | WO-0207705 A1 | 1/2002 |
| WO | WO-2004093848 A2 | 11/2004 |
| WO | WO-2005025540 A2 | 3/2005 |
| WO | WO-2005046636 A1 | 5/2005 |
| WO | WO-2005105043 A2 | 11/2005 |
| WO | WO-2008058691 A2 | 5/2008 |

OTHER PUBLICATIONS

Watling et al., European Journal of Pharmaceutical Sciences, 40: 352-358 (2010).*
"Excipients: Lactose Monohydrate." www.pformulate.com/lactoserev.htm. Accessed Jun. 18, 2012.
Clenil Compositum Polvere. Repertoro Farmaceutico Italiano. Milan: Framindustria: Associazione Nazionale dell'Industraia Farmaceutica. (1989):303-305. (Partial English Translation Included).
Endo et al. "Erythritol-Based Dry Powder of Glucagon for Pulmonary Administration." *Int. J. Pharm.* 290(2005):63-71.
Ohmori et al. "Development of Dry Powder Inhalation System of Novel Vasoactive Intestinal Peptide (VIP) Analogue for Pulmonary Administration." *Life Sci.* 79(2006):138-143.
Peart. "Electrostatic Charge Interactions in Pharmaceutical Dry Powder Aerosols." (1996).
Davies et al. "A Quantitative Assessment of Inhaled Drug Particle-Pulmonary Surfactant Interaction by Atomic Force Microscopy." *Colloids and Surfaces B: Biointerfaces.* 73(2009):97-102.
Hvorost. "Glycopyrronium Bromide." *Analysis of Drugs and Poisons.* mtnviewfarm.net/drugs-poisons-0799.html, retrieved Mar. 26, 2012.
Meggle Company Profile. Anshul Life Sciences. www.anshulindia.com, retrieved Mar. 26, 2012.

(Continued)

*Primary Examiner* — Kortney L Klinkel
*Assistant Examiner* — Lisbeth C Robinson
(74) *Attorney, Agent, or Firm* — Mintz Levin Cohn Ferris Glovsky and Popeo, P.C.; Muriel Liberto, Esq.

(57) ABSTRACT

The present invention relates to methods of making a powder for inhalation comprising a first step of mixing particles of a force-controlling agent selected from the group consisting of phospholipids, titanium dioxide, aluminum dioxide, silicon dioxide, starch, and salts of fatty acids, with particles of one or more pharmacologically active materials, wherein the mixing is achieved by one or more of the processes of sieving, mixing or blending, and wherein the mixing results in the particles of the force-controlling agent being disposed on the surface of the particles of the one or more pharmacologically active materials as either a particulate coating or as a continuous or discontinuous film.

**9 Cla

(56) References Cited

OTHER PUBLICATIONS

Podczeck. "The Relationship Between Physical Properties of Lactose Monohydrate and the Aerodynamic Behaviour of Adhered Drug Particles." *Int. J. Pharmaceutics*. 160(1998):119-130.

Smyth et al., eds. "Dissolution." *Controlled Pulmonary Drug Delivery*. New York: Springer. (2011): 22-23.

Kassem. "Generation of Deeply Inspirable Clouds from Dry Powder Mixtures." Ph.D. Thesis, Dept. Pharmacy, King's College University of London. (1990).
Meakin et al. "Simulated 'in-use' and 'mis-use' Aspects of the Delivery of Terbutaline Sulphate from Bricanyl Turbohaler™ Dry Powder Inhalers." *Int. J. Pharm*. 119(1995):103-108.
Reynolds, ed. *Martindale: The Extra Pharmacopeia*. London: The Pharmaceutical Press. (1993):1442.
van Kamp et al. "The Role of Water Uptake on Tablet Disintegration." *Pharm. Acta Helv*. 61.1(1986):22-29.
Wade et al. eds. "Magnesium Stearate." *Handbook of Pharmaceutical Excipients*. London: The Pharmaceutical Press. (1994):280-282.
Meakin et al. "The Effect on Flow Rate on Drug Delivery from the Pulvinal, a High-Resistance Dry Powder Inhaler." *J. Aero. Med*. 11.3(1998):143-152.
Peart et al. "Multicomponent Particle Interactions in Dry Powder Aerosols." *Pharma. Res*. 14.S11(1997):S142-S143. (Abstract #1405).

* cited by examiner

POWDER COMPOSITIONS FOR INHALATION

The present invention is concerned with powder formulations for use in dry powder inhalers (DPIs) and methods of forming such powder formulations.

Powder formulations typically consist of a binary mixture of small drug particles having a mean aerodynamic diameter of about 1 to 10 microns, and a coarser carrier material for said drug particles. These components are usually blended together to form a so-called "interactive mixture" wherein the finer drug particles are strongly adhered to the carrier particles. The use of interactive mixtures enables powders to be handled more easily during manufacture and during filling of the powder into DPI devices. Additionally, the small drug particles are maintained in a relatively dispersed state on the surface of the carrier particles.

When a DPI is actuated, the fine drug particles should detach from the carrier particles in order that they can be inhaled deep into a patient's respiratory tract. Depending on the nature of the drug substance and the carrier material, the force of adhesion can be strong or weak. If the force of adhesion is too strong, the detachment of fine drug particles from carrier particles can be very low and the resulting fine particle fraction of the dose emitted from a DPI can be very low as to be ineffectual. Powder engineers have developed several means by which they may influence this force of adhesion in order to produce interactive mixtures that possess a quality of adhesion that keeps the interactive mixture together during handling and storage, but which upon actuation of a DPI is not so strong as to prevent the efficient and reproducible re-dispersion of the drug into fine inhalable particles.

One such means is the use of a ternary component in the mixture. Such ternary components are often referred to in the art as force controlling agents or anti-adherent additives. The use of such additives in interactive mixtures is discussed in U.S. Pat. No. 6,521,260. Additives mentioned therein include amino acids, e.g. leucine, isoleucine, lysine, valine, methionine, phenylalanine, and salts of derivatives thereof such as aspartame or acesulfame K; peptides and polypeptides having molecular weight from 0.25 to 1000 KDa, and derivatives thereof; and phospholipids or derivative thereof, e.g. lecithin, more particularly soya lecithin; talc; titanium dioxide; aluminium dioxide; silicon dioxide; and starch.

Other very useful force controlling agents are the salts of fatty acids such as lauric acid, palmitic acid, stearic acid, erucic acid, behenic acid, or derivatives (such as esters and salts) thereof. Specific examples of such materials are: magnesium stearate; sodium stearyl fumarate; sodium stearyl lactylate; phospatidylcholines, phosphatidylglycerols and other examples of natural and synthetic lung surfactants; Liposomal formulations; lauric acid and its salts, for example, sodium lauryl sulphate, magnesium lauryl sulphate; triglycerides such as Dynsan 118 and Cutina HR; and sugar esters in general.

A particularly useful additive has been found to be magnesium stearate. The use of magnesium stearate in interactive mixtures is the subject of U.S. Pat. No. 6,645,466.

Interactive mixtures are usually formed by mixing or blending processes. A typical procedure consists of mixing a micronised drug substance with a powdered carrier material. Usually, the carrier material is pre-treated, for example the powder may be pre-blended in order to change its surface structure and therefore its surface energy in an attempt to manipulate the adhesion forces. When a ternary component is used, it is typical to treat the carrier with it, once again in order to influence the surface energy of the carrier particles.

The benefit of using magnesium stearate in dry powders is taught in U.S. Pat. No. 6,528,096. Specifically it teaches that it can be used to alter the surface properties of carrier particles and thereby improve the properties of dry powder formulations. This reference reports an "advantageous relationship" between surface coating carrier particles with magnesium stearate and the respirable fraction (fine particle fraction) of the emitted dose. Critical to the working of this invention is the need to ensure a continuous coating of magnesium stearate over more than 10% of the surface of the carrier particles. The requisite coating can be achieved by conventional blending of carrier and magnesium stearate, or alternatively mixing techniques applying higher shear forces can be employed. High shear mixing can achieve the requisite coating within about 0.5 hour, however, the skilled person is clearly taught that if conventional blending is to be employed the blending time must be in excess of 2 hours. In The Journal of Aerosol Medicine Vol 11, No. 3, 1998 at 143-152, an inventor of U.S. Pat. No. 6,528,096 teaches that pre-treatment of lactose particles with 0.25% magnesium stearate significantly improves the de-aggregation of beclamethasone dipropionate without causing segregation, i.e. separation of drug and carrier particles, during filling, transport or use.

In Pharmaceutical Research Vol 14, No 11 (Supplement), 1997 at pages S-142-S-143, the authors of whom one is an inventor of U.S. Pat. No. 6,528,096 teach that magnesium stearate was found to be an effective de-stabilizer by the proposed mechanism of reducing the electrostatic attraction force.

It is clear from the prior art that any beneficial properties that derive from the use of magnesium stearate are predicated on it coating carrier particles to some degree and thereby altering the surface properties of the particles. In this regard, the skilled person is taught that in order to advantageously influence the fine particle fraction of an emitted dose, the carrier particles should obtain a continuous or discontinuous surface coating of magnesium stearate. Certain mixing techniques are taught for achieving this result, which involve either high energy mixing, or long duration low energy mixing of magnesium stearates and carrier material. Other suggestions involve combining low energy blending coupled with carrier treatment steps involving high energy milling or mixing. Finally, Wagner et al in Pharmazie 60, 339-344 (2005) in studying the adhesion phenomena of interactive mixtures noted that the energetics of drug-to-carrier interactions are favourable compared to drug-to-drug interactions. This is rationalized on the basis that the fine drug particle sphere has greater contact with the surface of a much larger carrier particle (essentially sphere-to-plate contact) compared to the sphere-sphere contact of adjacent drug particles. Indeed, he reports that in fact, no drug-drug agglomerates were observed in the mixtures studied.

In summary, the prior art recognizes the problem of adhesion in interactive mixtures and suggests that the surface properties of the carrier material should be modified either mechanically or chemically by coating or partially coating with a ternary component. Nowhere is there a suggestion in the art to modify the surface properties of fine drug particles. Indeed, drug-drug interactions appear to be energetically unfavourable relatively speaking and it is perhaps not surprising that the art is concerned with treating carrier particles rather than treating the surface properties of drug particles. However, applicant has found that surface coating carrier particles with a ternary component does not always assure good blend homogeneity in interactive mixtures.

Applicant has now surprisingly found that powder formulations consisting of interactive mixtures of fine drug particles and carrier particles can be obtained if the fine drug particles are pre-treated with a force-controlling agent before blending with carrier particles to form an interactive mixture.

Accordingly, in a first aspect of the present invention there is provided a pharmacological powder for inhalation comprising fine drug particles and optionally carrier particles for supporting said drug particles, the formulation further containing a force-controlling agent, wherein the force-controlling agent is disposed on the surface of the fine drug particles as either a particulate coating, or as a continuous or discontinuous film.

The force-controlling agent of the present invention may be any material known for this purpose in the art. U.S. Pat. No. 6,521,260 discloses certain so-called force-controlling agents or anti-adherent additives that are useful in the present invention. These additives may be selected from amino acids, e.g. leucine, isoleucine, lysine, valine, methionine, phenylalanine, and salts of derivatives thereof such as aspartame or acesulfame K; peptides and polypeptides having molecular weight from 0.25 to 1000 KDa, and derivatives thereof; and phospholipids or derivative thereof, e.g. lecithin, more particularly soya lecithin; talc; titanium dioxide; aluminium dioxide; silicon dioxide; and starch.

However, preferred force-controlling agents are the salts of fatty acids such as lauric acid, palmitic acid, stearic acid, crude acid, behenic acid, or derivatives (such as esters and salts) thereof. Specific examples of such materials are: magnesium stearate; sodium stearyl fumarate; sodium stearyl lactylate; phospatidylcholines, phosphatidylglycerols and other examples of natural and synthetic lung surfactants; Liposomal formulations; lauric acid and its salts, for example, sodium lauryl sulphate, magnesium lauryl sulphate; triglycerides such as Dynsan 118 and Cutina HR; and sugar esters in general.

A more preferred force-controlling agent for use in compositions of the present invention is magnesium stearate. The amount of force-controlling agent employed should be at large enough to reduce the auto-adhesion force present between the drug particles. The upper limit depends on the toxicological acceptability of large amounts of force-controlling agent delivered to the lungs. A level of up to 2.0% is preferred. Within these limits, the amount of force-controlling agent employed will depend on the nature of the drug, and the drug loading. The skilled person will have regard the physical and chemical properties of the drug and be able to select an appropriate amount without undue burden or without having to resort to inventive activity.

In a particular embodiment a force-controlling agent, more particularly magnesium stearate may be employed in an amount of 0.01 to 2.0% by weight, more particularly 0.1 to 1.5% by weight, still more particularly 0.25 to 1.0% by weight, even more particularly 0.5 to 1.0% by weight. The fine drug particles covered by force-controlling agent particles or a film can be used per se since the auto-adhesion forces between drug particles can be largely reduced. However, if the bulk powder properties of any drug/force-controlling agent mixture are inappropriate for use in a dry powder inhaler, the mixture may be further formulated to a suitable powder composition by methods known to the skilled person from the prior art. The resulting powder for inhalation may be in form of a pelletized formulation or of an ordered mixture by adding a carrier material. The carrier material may be any carrier material that customarily finds use in dry powder formulations. As examples thereof, one can mention mono- or di-saccharides such as glucose, glucose mono-hydrate, lactose, lactose mono-hydrate, sucrose or trehalose; sugar alcohols such as mannitol or xylitol; polylactic acid or cyclodextrin; or mixtures thereof. Preferably lactose mono-hydrate is employed.

Any drug substance may be employed in a formulation according to the present invention. The force-controlling agent is employed in the manner described as means of disrupting inter-particulate forces between drug particles, and promoting the adhesion of drug particles to carrier particles thereby to form the desired interactive mixtures.

There are different types of inter-particulate forces present in bulk powders and their absolute size and relative contribution depend on the surface chemistry and physical characteristics of the particles in the bulk. A general description is given for example in F. Podczeck "Particle-particle Adhesion in Pharmaceutical Powder Handling", Imperial College Press, London 1998, pages 4-15. Hydrophilic interactions are larger than hydrophobic interactions and thus hydrophilic materials are less easy to disperse. This is owing to the capillary force that is generated due to interstitial moisture condensation between contiguous particles, which may be in evidence at ambient air relative humidity values of about 50%. In addition, porous hydrophilic particles often contain moisture trapped in pores. The capillary force generated by this mechanism is about 10 times stronger than other inter-particulate forces. Between particles of hydrophobic character, capillary forces are less in evidence, which means that strong inter-particulate especially present in hydrophilic compounds are generally not an issue for hydrophobic particles.

Also below a relative humidity value for ambient air of about 50% hydrophilic particles may show increased inter-particle adhesion because of absorbed moisture acting as a plasticizer. The plasticizing effect results in an increased contact area of the particles and therefore an increased Lifshitz-van der Waals inter-particulate force. From the above it is clear to one skilled in the art that drugs, which consist of soft hydrophilic particles are even more likely to be affected because the true area of contact between the particles may easily increase during storage and normal handling operations of bulk powder.

Hydrophilicity is the tendency of a compound to be solvated by water. More generally, hydrophilic compounds tend to adsorb readily water prior to solvation. The surface chemistry allows such compounds to be wetted readily, and particles of such compounds can form surface water films or layers. Hydrophilic materials are characterized by the fact that they possess a high surface tension value and have the ability to form hydrogen-bonds. There are many parameters that serve to define hydrophilic compounds. One such parameter is the octanol-water partition coefficient. Hydrophilic compounds have low values for this coefficient. In particular, hydrophilic drugs may be characterized for the purpose of the present invention as having a decadic logarithm of the octanol-water partition coefficient (Log P) smaller than 2, more particularly smaller than 1, even more particularly smaller than 0.5.

Another method of characterizing a hydrophilic drug is by measuring its contact angle against water. In particular, hydrophilic drugs for the purpose of the present invention may be characterized by a water contact angle smaller than 90°, more particularly smaller than 80°, even more particularly smaller than 70°.

Notwithstanding the generality of the present invention, having regard to the foregoing, the present invention is particularly advantageous when employed in the formulation of hydrophilic drugs.

The following drug substances in particular can be employed in formulations of the present invention:

Active substances may be chosen from beta-mimetics such as Levalbuterol, Terbutalin, Reproterol, Salbutamol, Salmeterol, Formoterol, Fenoterol, Clenbuterol, Bambuterol, Tulobuterol, Broxaterol, Indacaterol, Epinephrin, Isoprenaline or Hexoprenaline; an Anticholinergic such as Tiotropium, Ipratropium, Oxitropium or Glycopyrronium; a Corticosteroid, such as Butixocart, Rofleponide, Budesonide, Ciclesonide, Mometasone, Fluticasone, Beclomethasone, Loteprednol or Triamcinolone; a Leukotrienantagonist, such as Andolast, Iralukast, Pranlukast, Imitrodast, Seratrodast, Zileuton, Zafirlukast or Montelukast; a Phosphodiesterase-Inhibitor, such as Filaminast or Piclamilast; an PAF-Inhibitor, such as Apafant, Forapafant or Israpafant; a potassium channel opener such as Amiloride or Furosemide; a pain killer such as Morphine, Fentanyl, Pentazocine, Buprenorphine, Pethidine, Tilidine, Methadone or Heroin; a potency agent such as Sildenafil, Alprostadil or Phentolamine; or a pharmaceutically acceptable derivative or salt of any of the foregoing compounds or classes of compounds. In as much as any of these compounds possess chiral centres, the compounds can be used in optically pure form, or can be presented as diastereomeric mixtures or racemic mixtures. Dry powders of the present invention may also employ proteins, peptides, oligopeptides, polypeptides, polyamino acids nucleic acid, polynucleotides, oligo-nucleotides and high molecular weight polysaccharides. Examples of macromolecules that find use in the present invention are: —Albumins (preferably, human serum Insulin; albumin); BSA; IgG; IgM; insulin; GCSF; GMCSF; LHRH; VEGF; hGH; lysozyme; alpha-lactoglobulin; basic fibroblast growth factor basic fibroblast growth factor; (bFGF); asparaginase; tPA; urokinase-VEGF; chymotrypsin; trypsin; streptokinase; interferon; carbonic anhydrase; ovalbumin; glucagon; ACTH; oxytocin; phosphorylase b; alkaline phosphatase-secretin; vasopressin; levothyroxin; phatase; beta-galactosidase; parathyroid hormone, calcitonin; fibrinogen; polyaminoacids (e.g., DNAse, alphal antitrypsin; polylysine, polyarginine); angiogenesis inhibitors or pro-immunoglobulins (e.g., antibodies); moters; somatostatin and analogs; casein; collagen; gelatin; soy protein; and cytokines (e.g., interferon, interleukin); immunoglobulins;

Physiologically active proteins such as peptide hormones, cytokines, growth factors, factors acting on the cardiovascular system, factors acting on the central and peripheral nervous systems, factors acting on humoral electrolytes and hemal substances, factors acting on bone and skeleton, factors acting on the gastrointestinal system, factors acting on the immune system, factors acting on the respiratory system, factors acting on the genital organs, and enzymes;

Hormones and hormone modulators including insulin, proinsulin, C-peptide of insulin, a mixture of insulin and C-peptide of insulin, hybrid insulin cocrystals (Nature Biotechnology, 20, 800-804, 2002), growth hormone, parathyroid hormone, luteinizing hormone-releasing hormone (LH-RH), adrenocorticotropic hormone (ACTH), amylin, oxytocin, luteinizing hormone, (D-Tryp6)-LHRH, nafarelin acetate, leuprolide acetate, follicle stimulating hormone, glucagon, prostaglandins, estradiols, testosterone, and other factors acting on the genital organs and their derivatives, analogues and congeners. As analogues of said LH-RH, such known substances as those described in U.S. Pat. Nos. 4,008,209, 4,086, 219, 4,124,577, 4,317,815 and 5,110,904 can be mentioned;

Hematopoietic or thrombopoietic factors include, among others, erythropoietin, granulocyte colony stimulating factor (G-CSF), granulocyte-macrophage stimulating factor (GM-CSF) and macrophage colony stimulating factor (M-CSF), leukocyte proliferation factor preparation (Leucoprol, Morinaga Milk), thrombopoietin, platelet proliferation stimulating factor, megakaryocyte proliferation (stimulating) factor, and factor VIII;

Therapeutic factors acting on bone and skeleton and agents for treating osteoporosis including bone GLa peptide, parathyroid hormone and its active fragments (osteostatin, Endocrinology 129, 324, 1991), histone H4-related bone formation and proliferation peptide (OGP, The EMBO Journal 11, 1867, 1992) and their muteins, derivatives and analogs thereof;

Enzymes and enzyme cofactors including pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, and superoxide dismutase (SOD);

Vaccines include Hepatitis B, MMR (measles, mumps, and rubella), and Polio vaccines;

Growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), and hepatocyte growth factor (HGF);

Factors acting on the cardiovascular system including factors which control blood pressure, arteriosclerosis, etc., such as endothelins, endothelin inhibitors, endothelin antagonists described in EP 436189, 457195, 496452 and 528312, JP [Laid Open] No. H-3-94692/1991 and 130299/1991, endothelin producing enzyme inhibitors vasopressin, renin, angiotensin I, angiotensin II, angiotensin III, angiotensin I inhibitor, angiotensin II receptor antagonist, atrial naturiuretic peptide (ANP), and antiarrythmic peptide; Factors acting on the central and peripheral nervous systems including opioid peptides (e.g. enkephalins, endorphins), neurotropic factor (NTF), calcitonin gene-related peptide (CGRP), thyroid hormone releasing hormone (TRH), salts and derivatives of TRH [JP [Laid Open]No. 50-121273/1975 (U.S. Pat. No. 3,959, 247), JP [Laid Open]No. 52-116465/1977 (U.S. Pat. No. 4,100,152)], and neurotensin;

Factors acting on the gastrointestinal system including secretin and gastrin;

Factors acting on humoral electrolytes and hemal substances including factors which control hemagglutination, plasma cholesterol level or metal ion concentrations, such as calcitonin, apoprotein E and hirudin. Laminin and intercellular adhesion molecule 1 (ICAM 1) represent exemplary cell adhesion factors;

Factors acting on the kidney and urinary tract including substances which regulate the function of the kidney, such as brain-derived natriuretic peptide (BNP), and urotensin;

Factors which act on the sense organs including factors which control the sensitivity of the various organs, such as substance P;

Chemotherapeutic agents, such as paclitaxel, mytomycin C, BCNU, and doxorubicin;

Factors acting on the immune system including factors which control inflammation and malignant neoplasms and factors which attack infective microorganisms, such as chemotactic peptides and bradykinins; and Naturally occurring, chemically synthesized or recombinant peptides or proteins which may act as antigens, such as cedar pollen and ragweed pollen, and these materials alone or together with coupled to haptens, or together with an adjuvant.

The present invention is particularly useful in the formulation of hydrophilic and moisture sensitive active substances, such as the salt forms of any of the compounds mentioned above such as the chloride, bromide, iodide, nitrate, carbonate, sulphate, methylsulphate, phosphate, acetate, benzoate, benzensulphonate, fumarate, malonate, tartrate, succinate, citrate, lactate, gluconate, glutamate, edentate, mesylate, pamoate, pantothenate or hydroxynaphthoate; or an ester form such as an acetate, propionate, phosphate, succinate or etabonate.

Formulations containing a beta-mimetic, an anti-cholinergic or a corticosteroid, alone or in any combination thereof constitute preferred embodiments of the present invention. These actives may be present in salt or ester form, such as a beta-mimetic in salt form, e.g. levalbuterol sulphate, formoterol fumarate, formoterol tartrate, salbutamol sulphate or salmeterol xinafoate (salmeterol 1-hydroxy-2-naphthoate); or a corticosteroid in the form of an ester, such as beclamethasone dipropionate, fluticasone propionate, triamcinoline 16,21-diacetate, triamcinoline acetonide 21-acetate, triamcinoline acetonide 21-disodium phosphate, triamcinoline acetonide 21-hemisuccinate, mometasone furoate, or loteprednol etabonate.

In a most preferred embodiment of the present invention the formulation contains an anti-cholinergic agent in salt form such as oxitropium bromide, glycopyrronium bromide (glycopyrrolate), ipratropium bromide or tiotropium bromide.

In another aspect of the present invention there is provided a method of treating a medical condition comprising administering to a patient in need thereof a pharmacological powder of the present invention. Said powder may suitably be administered to parenterally to an human patient, in particular by inhalation, using, for example, a DPI.

A method of formulating powder formulations hereinabove described forms yet another aspect of the present invention.

The formulations of the present invention may be prepared in such a manner that the drug is first brought in contact with the appropriate amount of force-controlling agent. Close contact of particles of force-controlling agent with drug particles is necessary and important to achieve a reduction of the auto-adhesion forces established in the bulk drug powder. The close contact can be achieved by methods known to the skilled person. Particularly, screening both drug and agent through a narrow sieve gives a neat dispersion of both particle populations. Appropriately sized sieves for this operation are e.g. 25 to 250 micrometer size (500 to 60 mesh according to BS 410), more particularly 25 to 180 micrometer (500 to 85 mesh according to BS 410), even more particularly 25 to 90 micrometer (500 to 170 mesh according to BS 410).

Additionally or alternatively, blending and mixing apparatus may be applied to achieve close inter-particle contact, for example tumble blenders, bin blenders, conical blenders and the like. High shear mixers can also be used if the auto-adhesive properties of the drug particles are so that high shear forces are required together with use of a force-controlling agent for forming a surface-energy-reducing particulate coating or film. Particularly, tumble blending may be applied for this purpose.

If the fine drug particles to be formulated as a powder formulation for inhalation are not of the appropriate size suitable for the inhaled route, particle reduction techniques in the presence of force-controlling agent can be applied to yield particles of suitable size. The preferred method is co-micronisation using an air jet mill which again brings the drug particles and the particles of force-controlling agent in such a contact that either a continuous or discontinuous film is formed or the agent particles adhere to the drug particle surface. However, any technique known in the art and suitable for co-micronisation can be employed.

Accordingly, the invention provides in another of its aspects a method of producing powder formulations containing fine drug particles comprising the step of blending one or more pharmacologically active compound with a force-controlling agent in a powder blender. In yet another aspect of the present invention there is provided a method of producing powder formulations containing fine drug particles comprising the step of co-micronising one or more pharmacologically active compound with a force-controlling agent. Preferred powder blenders include diffusion blenders and tumble blenders.

The blending step described above is preferably carried out as one of a series of blending steps described below.

In a first step, one or more drugs and force-controlling agent are mixed together in such a way that the agent adheres to the surface of the drug particles either as a particulate coating or as a continuous or discontinuous film. As stated hereinabove, the treated drug particles may possess appropriate properties that enable them to be used alone in a dry powder inhaler device. However, if desired they may be further mixed with a carrier material.

Accordingly, in an optional step the treated fine drug particles are mixed with a carrier material. This mixing step is preferably carried out in a powder blender for a period not exceeding one hour and preferably less than 30 minutes, more particularly less than 20 minutes, for example about 15 to 20 minutes.

The carrier material may be used untreated or it may be treated in the same manner as the fine drug particles.

In the methods of the present invention, the drug, force-controlling agent and carrier material can be as stated already herein above.

If the amount of drug used in the formulation is low, e.g. less than about 30% by weight of the formulation, more particularly about 1% to 20% by weight, even more particularly about 0.01 to 10% by weight of the formulation, it is preferred that after the treatment of the fine drug particles, the resulting drug/force-controlling agent mixture is blended with a small portion of the carrier material, e.g. about 10%, to form a powder mixture relatively concentrated with respect to the drug. This is to ensure adequate mixing of the drug with the carrier material. Subsequently, an additional step is employed to mix the remaining carrier material with the concentrated mixture from the earlier step. Again, this is preferably carried out in a powder blender. It is preferred that no other blending step is carried out. However, it may be deemed necessary to perform additional blending and sieving steps to achieve a final powder formulation of suitable quality.

To ensure the powder ingredients are of the appropriate particle size it is customary to prepare the ingredients by screening through appropriate sized sieves, e.g. 25 to 500 micrometer size (500 to 30 mesh according to BS 410), more particularly 63 to 250 micrometer (240 to 60 mesh according to BS 410).

In order that the fine drug particles are inhalable, i.e. in order that they can pass into the deep lung such as the terminal and respiratory bronchioles and the alveolar ducts and sacs, they must be in particulate form having a mean particle diameter (measured as the mass mean aerodynamic diameter) of at most about 10 micrometers, e.g. from 1 to 10 micrometers, and preferably 1 to 6 micrometers, even more preferably 1 to 4 micrometers. Such micro-fine particles can be obtained in a manner known per se, for example by micronisation, controlled precipitation from selected solvents, or by spray drying.

The amount of drug employed may vary within wide limits depending on the nature of the drug, the type and severity of the condition to be treated and the condition of the patient in need of treatment.

For drugs employed to treat local conditions of the lung such as all manner of asthma and chronic obstructive pulmonary disease, relatively low doses of drug can be employed, for example about 5 to 5000 micrograms, more particularly 5 to 500 micrograms. For drugs that are intended to be delivered systemically through the lung, one may need higher doses to take into account issues relating to absorption through the lung and into the blood plasma. Typically, one might employ drugs at levels of about 20 micrograms to 50 milligrams, more particularly 50 micrograms to 20 milligrams.

Expressed as a concentration based on the total weight of the formulation, the drug may be present in amounts of 0.01 to 30% by weight, more particularly 0.1 to 10% by weight, more particularly 0.1 to 5% by weight. It is not surprising therefore that to achieve dosage accuracy, the drug must be diluted with carrier material. In a typical formulation the carrier material may be present in amounts of up to 99% by weight or more, in particular 50 to 99% by weight, depending on the particular dilution desired and on the amount of force-controlling agent employed in the formulation. The dilution is chosen such that an acceptable shot weight delivered from an inhaler contains exactly the desired dose of drug. In this regard, the exact dose may be delivered in a single shot or multiple shots. Dilution is also used to affect powder mixtures having good macroscopic properties such as flowability, and to balance adhesive or cohesive forces of the micro-fine active substance to ensure good homogeneity of the formulation.

Nucleic acids, including double-stranded or single-stranded polynucleotide, oligonucleotide or short nucleic acid sequences may also be formulated according to the present invention. The term nucleic acid includes both RNA (e.g. siRNA, mRNA, ribozymes, aptamers) and DNA (e.g. cDNA or genomic DNA). The nucleic acid may be present in the form of a vector (e.g. a plasmid or other construct) with suitable sequences to direct or control expression (i.e. a promoter sequence).

Carrier materials employed must be in the form of sufficiently large particle size such that they can be easily handled during manufacture and filling operations. They should also be large enough such that they are not inhalable into the deep lung. Typically a carrier material will have a mean particle diameter (measured as the mass mean aerodynamic diameter) of about 10 to 500 micrometers, and preferably 50 to 300 micrometers.

Dry powder formulations of the present invention are particularly suitable for use in multi-dose dry powder inhalers. In particular, the formulations are suitable for use in such inhalers, which comprise a reservoir from which individual therapeutic dosages can be withdrawn on demand through actuation of the device. However, formulations of the present invention are also useful in multi-dose inhalers that contain a plurality of capsules containing single or multiple pre-dosed units.

Typical of such multi-dose inhaler device suitable for use with formulations of the present invention is described in U.S. Pat. No. 6,182,655, which is hereby incorporated by reference in its entirety.

In yet another aspect of the present invention there is provided a method of treating a medical condition comprising administering to a patient in need thereof a pharmacological powder made in accordance with the method of the invention.

The present invention in another of its aspects is directed to such multi-dose inhalers containing the formulation of the present invention.

Multi-dose inhalers may contain a reservoir of dry powder that contains tens or even hundreds of therapeutic doses. The term "therapeutic dose(s)" as used herein means an amount of inhalation formulation containing a requisite amount of drug to illicit a therapeutic effect, e.g. to alleviate, prevent or inhibit the particular condition to be treated, when delivered to a patient. A therapeutic dose may be delivered with one or more actuations of a DPI device. This is because the amount of powder that can be delivered to a patient without irritating the patient, e.g. making the patient cough, or what can reasonably or comfortably be delivered within a single inspiration, is limited to about 50 mg per actuation, more particularly 25 mg per actuation. Accordingly, depending on the nature of the drug and the nature and severity of the condition to be treated, one or more actuations may be necessary per number of hours, per day, for any number of days, weeks, months and so-forth.

The therapeutic dose will depend largely on the nature of the drug, the condition of the patient, and the nature and severity of the condition to be treated. A therapeutic dose may range between as little as 1 ng/kg, for example when treating a local condition such as asthma with a potent active substance to as much as 10 mg/kg, more particularly dose will range from 20 ng/kg to 1 mg/kg. The therapeutic dose will be indicated on packaging or labelling accompanying the DPI device and is specifically referred to in the Label Claim.

In order to ensure inter-batch quality and reproducibility, formulations should be tested in order to ensure that the mean dose of formulation emitted from a MDI, should not vary considerably from the Label Claim. In this regard, the formulations of the present invention are particularly stable, for example they meet the following standards:

The Mean Delivered Dose is within +/−15% of the Label Claim, and 9 from 10 at least of single doses are not outside +/−25% of the mean, and all single doses are within +/−35% of the mean; or At least 9 from 10 single doses are within +/−20% of the Label Claim, and all single doses are within +/−25% of the Label Claim.

The Shot Weight and Delivered Dose and their variance can be measured using the Dosage Unit Sampling Apparatus (DUSA). The fine particle fraction (FPF) can be measured using an Andersen Cascade Impactor (ACI). The measurement methodology and the apparatus therefore are well known in the art, and are described in the United States Pharmacopoeia Chapter <601>, or in the inhalants monograph of the European Pharmacopoeia, both of which documents are hereby incorporated by reference. The USP states that the Apparatus 1 should be used for the measurement of FPF. The USP also states that Delivered Dose Uniformity should be measured with DUSA or its equivalent. However, the Delivered Dose and Delivered Dose uniformity are preferably measured using the so-called Funnel Method. The Funnel Method is described in *Drug Delivery to the Lungs, VIII* p 116 to 119, which is hereby incorporated by reference. In summary, the Funnel Method consists of discharging a formulation from a DPI into a Funnel Apparatus, which basically consists of a standard Buchner Funnel. The discharged dose is captured on the glass sinter of the Funnel, and can be washed off, and the dose determined using HPLC analysis. The Funnel Method gives comparable results to the standard USP apparatus, and is generally considered to be an equivalent of the DUSA apparatus. Fine particle fraction measured according to the above described methodology is considered to consist of the combined fractions collected from stages 2 to Filter Stage of an Andersen Cascade Impactor calibrated at 60 L/min air flow rate. These fractions have an aerodynamic particle size of less than 3.2 micrometers.

Alternatively, Fine Particle Fraction can be measured by the Twin Impinger Method and the Multi-stage Liquid Impinger Method as are described in the Pharmacopoeia, and as are set forth in the Examples below.

Formulations of the present invention meet pharmacopoeia requirements as to Delivered Dose Uniformity as set forth, for example in the United States and European Pharmacopoeias. For example, formulations of the present invention meet the requirement set out in the USP26-NF21 chapter <601> "Delivered Dose Uniformity". Indeed, the formulations appear to be so stable that they may even meet the relatively more stringent Delivered Dose Uniformity requirements set forth in the current Draft Guidance from the FDA, published by the CDER in October 1998. Still further, the Delivered Dose of the formulations contains a high fraction of fine particles, i.e. particles that are capable of penetrating the deep lung, e.g. having a diameter of less than about 4.7 micrometers, as measured by the ACI; below 6.4 as measured by the Twin Impinger; and below 6.8 as measured by the Multi-stage Liquid Impinger.

There now follows a series of examples that serve to illustrate the invention.

Method Particle Fraction Size Measurement Method

Assemble the Andersen Cascade Impactor according to manufacturer's instructions with a suitable filter in place and ensure that the system is airtight. To ensure efficient particle capture, coat each plate with a high viscosity liquid deposited from a volatile solvent. The pre-separator should be coated in the same way or should contain 10 ml of a suitable solvent. Connect the apparatus to a flow system comprising flow control valve, two-way valve, timer and vacuum pump.

The test is conducted at a flow rate adapted to the internal resistance of the inhaler device drawing 4 liters of air through the apparatus. At high flow rates it may be necessary to remove the lowest stages from the stack. For adjustment of the flow rate connect a flow meter, calibrated for the volumetric flow leaving the meter, to the induction port. Adjust the flow control valve to achieve steady flow through the system at the required rate.

Ensure that critical flow occurs in the flow control valve by measuring the absolute pressure on both sides of the flow control valve. Switch off the airflow.

Prepare the dry-powder inhaler for use according to the patient instructions. With the pump running and the two-way valve closed, locate the mouthpiece of the inhaler in the mouthpiece adapter. Discharge the powder into the apparatus by opening the valve for the time required for drawing 4 liters of air through. Repeat the discharge sequence. The number of discharges should be minimised and typically would not be greater than ten. The number of discharges should be sufficient to ensure an accurate and precise determination of fine particle dose. After the final discharge, wait for 5 seconds and then switch off the pump.

Dismantle the apparatus. Carefully remove the filter and extract the active ingredient into an aliquot of the solvent. Remove the pre-separator, induction port and mouthpiece adapter from the apparatus and extract the drug into an aliquot of the solvent. Extract the active ingredient from the inner walls and the collection plate of each of the stages of the apparatus into aliquots of solvent. Using a suitable method of analysis, determine the quantity of drug contained in each of the nine volumes of solvent.

Calculate the mass of drug deposited on each stage per discharge and the mass of drug per discharge deposited in the induction port, mouthpiece adapter and where used the pre-separator. The total mass of the drug is not less than 75 per cent and not more than 125 per cent of the average delivered dose determined during testing for uniformity of delivered dose. If the total mass is outside this range the test must be repeated.

Starting at the filter, derive a cumulative mass vs. cut-off diameter of the respective stages. Calculate the Fine Particle Dose (FPD) by interpolation the mass of drug less than 5 μm. If necessary, and where appropriate, plot the cumulative fraction of drug versus cut-off diameter on log probability paper, and use this plot to determine values for the Mass Median Aerodynamic Diameter (MMAD) and the Geometric Standard Deviation (GSD).

EXAMPLE 1

Formulation 1

A powder formulation consisting of glycopyrrolate (glycopyrronium bromide), magnesium stearate and lactose monohydrate is formed as follows: Glycopyrrolate and magnesium stearate are screened through a 38 micrometer sieve. Lactose monohydrate is screened through a 250 micrometer sieve. The sieved glycopyrrolate-magnesium stearate bulk powder is mixed with about half the amount of sieved lactose monohydrate in a Turbula T2C powder blender at 22 rpm for 10 minutes.

The resulting concentrated mixture is sieved through a 250 micrometer sieve, the remaining lactose monohydrate is added and the mixture blended for a further 10 minutes at 22 rpm in the blender.

The dry powder blend achieved is homogeneous when assessed visually and under the microscope. The blend has satisfying blend homogeneity with a relative standard deviation of the drug content of the withdrawn samples below 5%, usually even below 3%.

Formulation 2

For Comparison, Not Part of the Invention

A dry powder formulation consisting of glycopyrrolate (glycopyrronium bromide), magnesium stearate and lactose monohydrate is formed according to a prior art process as follows: Lactose monohydrate and magnesium stearate are screened through a 250 micrometer sieve and mixed in a Turbula T2C powder blender at 30 rpm for 20 minutes.

Glycopyrrolate and about half of the lactose-magnesium stearate mixture are screened through a 250 micrometer sieve and mixed in a Turbula T2C powder blender at 46 rpm for 20 minutes.

Eventually, the resulting concentrated mixture and the remaining lactose monohydrate are sieved through a 250 micrometer sieve and the mixture blended for a 10 minutes at 46 rpm in the blender.

The dry powder blend achieved has an inhomogeneous aspect when assessed visually and under the microscope. The blend homogeneity test gives a relative standard deviation of the drug content of the withdrawn samples of more than 5%.

EXAMPLE 2

Formulation 3

A dry powder formulation consisting of glycopyrrolate (glycopyrronium bromide), magnesium stearate and lactose monohydrate is formed according to the following method: Glycopyrrolate and magnesium stearate are screened through a 38 micrometer sieve. Lactose monohydrate is screened through a 250 micrometer sieve. Both sieved bulk powders are mixed in a high shear mixer Niro PP1 for 10 minutes at 300 rpm impeller speed and 300 rpm chopper speed.

The powder blend achieved is homogeneous when assessed visually and under the microscope. The blend has satisfying blend homogeneity with a relative standard deviation of the drug content of the withdrawn samples below 5%, usually even below 3%.

EXAMPLE 3

Measurement of Fine Particle Fraction

The formulations 1 and 2 employed are those formed according to Example 1 above. The powder blends thus produced are filled into SkyePharma proprietary dry powder inhalers Skyehaler™ as more fully described in U.S. Pat. No. 6,182,655 for assessment of Dose Content Uniformity and fine particle fraction of the delivered dose.

After filling the formulations in the DPI devices, the devices are allowed to stand for at least 24 hours before testing.

The aerodynamic particle size distribution is determined using the Andersen Cascade Impactor Mark II, equipped with pre-separator and 8 stages, designed and calibrated for 60 L/min flow rate (apparatus D of the Eur. Pharmacopoeia 4.4 section 2.9.18). The fine particle dose is the amount of drug that is found on the stages 2 to the filter stage of this apparatus.

3 actuations of the formulations of Example 1 and 2 are discharged into the particle sizing apparatus specified above by pulling 4 L of air through the apparatus at a set flow rate of 60 L/min. Delivered and aerosolised drug particles are classified in accordance with their particle momentum achieved in the flow which depends on the equivalent aerodynamic particle size. Thus fractions of the dose are deposited at different parts or collecting stages of the apparatus, in accordance with the aerodynamic particle size of the drug particles. Each fraction is collected, adjusted to volume and analysed using HPLC.

HPLC analysis of Formulation I showed that the fine particle fraction (less than 3.2 micrometers) of the dose delivered into the Andersen Cascade Impactor apparatus is about 42%.

HPLC analysis of Formulation 3 showed that the fine particle fraction (less than 3.2 micrometers) of the dose delivered into the Andersen Cascade Impactor apparatus is about 43%.

What is claimed is:

1. A method of making a powder for inhalation consisting of a first step (a) of mixing particles of a force-controlling agent selected from magnesium stearate, with particles of one or more pharmacologically active materials,
   wherein the mixing is achieved by one or more of the processes of sieving or blending, wherein the blending is not carried out in a high shear mixer
   wherein the mixing results in the particles of the force-controlling agent being disposed on the surface of the particles of the one or more pharmacologically active materials as either a particulate coating or as a continuous or discontinuous film; and a second step of
   (b)(1) sieving or blending the powder obtained in step (a) with 50-99 weight percent of a carrier material based on the total weight of the formulation, or
   (b)(2) blending the powder obtained in step (a) with a first portion of a carrier material to form a second mixture, and in a subsequent step mixing the remainder of the carrier material with said second mixture,
   said carrier material having a particle size of 50-500 µm,
   wherein the particles of one or more pharmacologically active materials comprise particles of an anti-cholinergic drug in salt form selected from the group consisting of oxitropium bromide, glycopyrronium bromide, ipratropium bromide and tiotropium bromide.

2. The method of claim 1, wherein the second step is step (b)(2), blending the powder obtained in step (a) with a first portion of a carrier material to form a second mixture, and in a subsequent step mixing the remainder of the carrier material with said second mixture.

3. The method of claim 1 or 2, wherein the blending is carried out in a diffusion blender, tumble blender, bin blender, or conical blender.

4. The method of claim 1, wherein the force-controlling agent is present in amounts of up to 5.0% by weight based on the total weight of the formulation.

5. The method of claim 1, wherein the force-controlling agent is present in amounts of 0.01 to 5.0% by weight based on the total weight of the formulation.

6. The method of claim 1, wherein the carrier material is selected from glucose, lactose, lactose mono-hydrate, sucrose, trehalose, mannitol, xylitol, polylactic acid, or mixtures thereof.

7. The method of claim 6, wherein the carrier material is lactose mono-hydrate.

8. The method of claim 1, wherein the one or more pharmacologically active materials is selected from the group consisting of pharmacologically active materials having a contact angle against water that is less than 90°.

9. The method of claim 1, wherein the one or more pharmacologically active materials is selected from the group consisting of pharmacologically active materials having an octanol-water partition coefficient (log P) smaller than 2.

* * * * *